(12) United States Patent
Zeng et al.

(10) Patent No.: US 9,895,222 B2
(45) Date of Patent: Feb. 20, 2018

(54) AORTIC REPLACEMENT VALVE (71) Applicant: Horizon Scientific Corp., Irvine, CA (US)

(72) Inventors: Min Frank Zeng, Irvine, CA (US); Pham Lo, Irvine, CA (US)

(73) Assignee: Venus Medtech (Hangzhou) Inc. (CN)

( * ) Notice: Subject to any disclaimer, the term of this patent is extended or adjusted under 35 U.S.C. 154(b) by 163 days.

(21) Appl. No.: 14/828,234

(22) Filed: Aug. 17, 2015

(65) Prior Publication Data
US 2017/0049566 A1 Feb. 23, 2017

(51) Int. Cl.
*A61F 2/24* (2006.01)

(52) U.S. Cl.
CPC .......... *A61F 2/2418* (2013.01); *A61F 2/2436* (2013.01); *A61F 2/2409* (2013.01); *A61F 2210/0014* (2013.01)

(58) Field of Classification Search
CPC ........ A61F 2/24; A61F 2/2448; A61F 2/2445; A61F 2/2418; A61F 2/2412
USPC .................................................. 623/2.1–2.19
See application file for complete search history.

(56) References Cited

U.S. PATENT DOCUMENTS

| | | | | |
|---|---|---|---|---|
| 9,532,868 B2* | 1/2017 | Braido | .................. | A61F 2/2418 |
| 2015/0105856 A1* | 4/2015 | Rowe | .................. | A61F 2/2409 |
| | | | | 623/2.18 |
| 2015/0142104 A1* | 5/2015 | Braido | .................. | A61F 2/2418 |
| | | | | 623/2.18 |
| 2015/0157455 A1 | 6/2015 | Edwards | | |
| 2015/0209137 A1* | 7/2015 | Quadri | .................. | A61F 2/2418 |
| | | | | 623/2.11 |
| 2015/0209141 A1* | 7/2015 | Braido | .................. | A61F 2/2418 |
| | | | | 623/2.17 |
| 2015/0216661 A1 | 8/2015 | Hacohen et al. | | |
| 2015/0327994 A1* | 11/2015 | Morriss | .................. | A61F 2/2418 |
| | | | | 623/2.17 |
| 2015/0359629 A1* | 12/2015 | Ganesan | ............... | A61F 2/2409 |
| | | | | 623/2.11 |
| 2016/0038281 A1* | 2/2016 | Delaloye | ............... | A61F 2/2409 |
| | | | | 623/2.18 |
| 2016/0045165 A1* | 2/2016 | Braido | ................. | A61B 5/6862 |
| | | | | 623/2.1 |
| 2016/0135950 A1* | 5/2016 | Braido | .................. | A61F 2/2412 |
| | | | | 623/2.17 |
| 2016/0199180 A1* | 7/2016 | Zeng | ..................... | A61F 2/2418 |
| | | | | 623/2.17 |
| 2016/0199183 A1* | 7/2016 | Braido | .................. | A61F 2/2412 |
| | | | | 623/2.18 |

(Continued)

OTHER PUBLICATIONS

PCT Search Report and Opinion dated Oct. 28, 2016 from PCT/US2016/047261.

*Primary Examiner* — Suzette J Gherbi
(74) *Attorney, Agent, or Firm* — Raymond Sun (57) ABSTRACT

A heart valve assembly has a frame comprising an inflow section, an outflow section, and a connecting section that is located between the inflow section and the outflow section. The inflow section has a plurality of legs that extend radially outwardly, and the connecting section has a greater flexibility than the inner section. The assembly also includes a plurality of leaflets coupled to the connecting section, a valve skirt extending from the leaflets towards the inflow section of the frame, and a cuff section, with the legs and the cuff section together defining a cuff for engagement with a native annulus.

20 Claims, 10 Drawing Sheets

(56) References Cited

U.S. PATENT DOCUMENTS

2016/0310267 A1\* 10/2016 Zeng ................... A61F 2/2418
2016/0317305 A1\* 11/2016 Pelled ............... B29C 66/53245

\* cited by examiner

AORTIC REPLACEMENT VALVE

BACKGROUND OF THE INVENTION

1. Field of the Invention

The present invention is directed to an aortic replacement valve, as well as methods and systems for transcatheter placement of the aortic replacement valve.

2. Description of the Prior Art

There are many aortic replacement valves that are available for trans-catheter replacement of a defective aortic valve. The current aortic valve designs are made of a metal frame with tissue valves, and skirt sutured on to the frame. The frame is mostly a skeleton-type design, allowing it to be crimped to a small profile for insertion and expansion in situ.

Unfortunately, the current aortic valve designs still suffer from some important drawbacks.

First, coronary access remains an issue. With the wire braided or slotted tube designs utilized by the current aortic valve frames, the cells are condensely-packed to achieve the required expansion force. The condensed cells could be too small to allow for catheters to pass through, and thereby make the later coronary access by catheters (for angioplasty and stenting) more difficult.

Second, there is often a need to resheath the partially deployed valve assembly. The current aortic valves are either not retrievable upon partial deployment at regular body temperature due to its expansion force, or are retrievable only by reducing the frame's expansion force. In the latter situation, the reduced expansion force limits the suitability of the valve assembly to replacement of severely calcified native valves.

Third, perivalvular leak (PVL) is still a problem with many of the existing transcatheter aortic valve assemblies. Many of the first generation valve assemblies did not address the PVL issue. The later generations started to add features, such as cuffs, to the inflow section. The cuff is essentially a separate component attached to the frame on the outside. However, adding such cuffs increases the profile of the valve assembly when crimped, thereby requiring a larger delivery system.

Thus, there remains a need for a transcatheter aortic valve assembly that overcomes the shortcomings described above.

SUMMARY OF THE DISCLOSURE

The present invention provides a way to make the valve assembly retrievable upon its deployment by up to two thirds of its length. Also, upon the expansion of its inflow end in the annulus, the valve assembly will form a soft cuff surrounding the inflow end to seal the gaps between the valve assembly and the annulus.

The present invention accomplishes these objectives by providing a heart valve assembly having a frame comprising an inflow section, an outflow section, and a connecting section that is located between the inflow section and the outflow section. The inflow section has a plurality of legs that extend radially outwardly, and the connecting section has a greater flexibility than the inner section. The assembly also includes a plurality of leaflets coupled to the connecting section, a valve skirt extending from the leaflets towards the inflow section of the frame, and a cuff section, with the legs and the cuff section together defining a cuff for engagement with a native annulus.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1A:
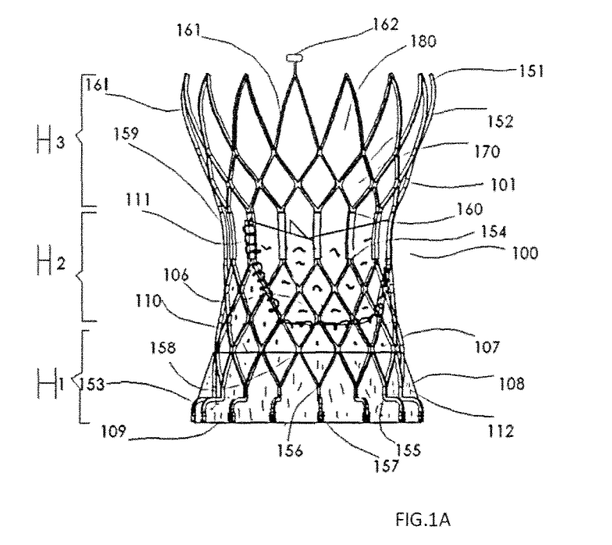
FIG. 1A is a perspective side view of an aortic valve assembly according to one embodiment of the present invention shown in an expanded configuration.
Figure 1B:
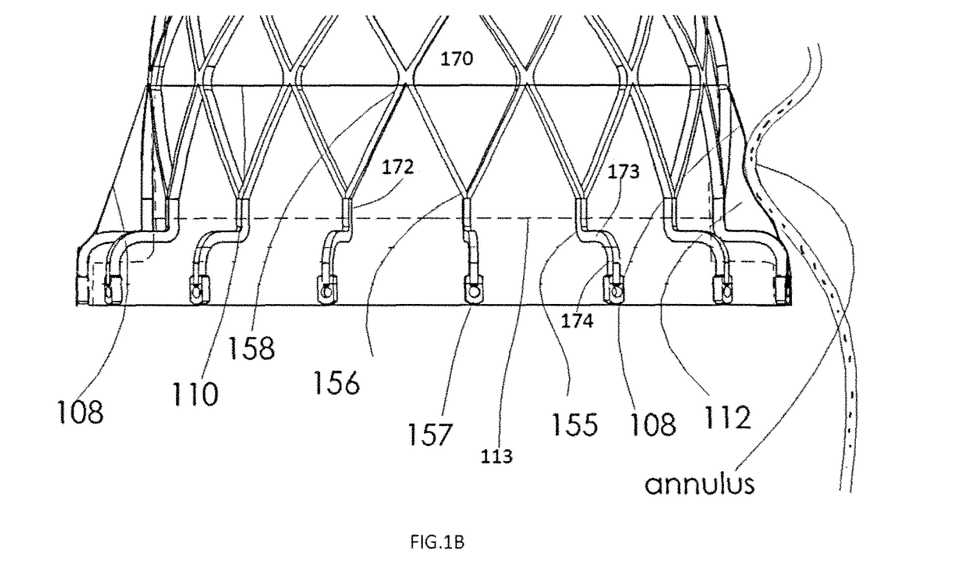
FIG. 1B is an enlarged side view of the inflow end of the assembly of FIG. 1A.
Figure 2:
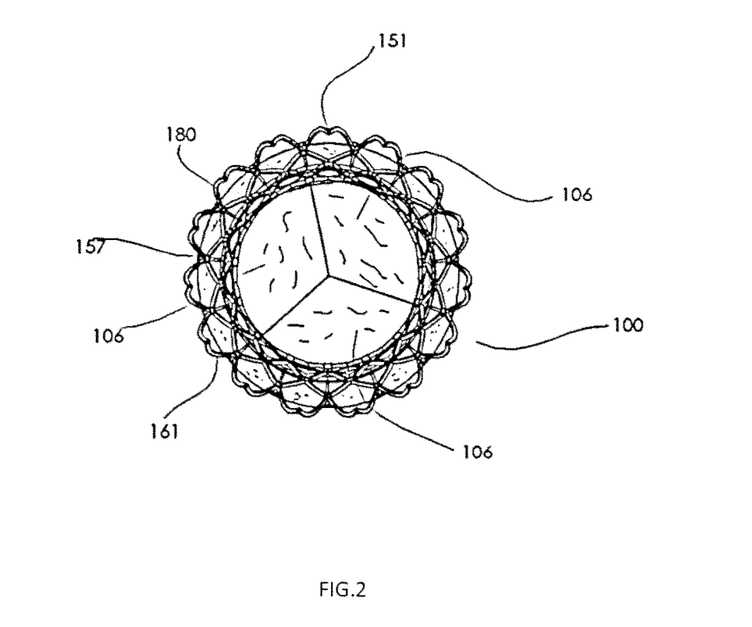
FIG. 2 is a top view of the assembly of FIG. 1A.

The present invention provides an aortic replacement valve assembly 100 that is shown in fully assembled form in FIGS. 1A, 1B and 2. The assembly 100 has a frame 101 (see FIGS. 3-5) that has an inflow section IS and an outflow section OS that is connected by a connecting section CS. The assembly 100 also has an integrated leaflet and skirt assembly 102 (see FIGS. 6-8) that comprises a plurality of leaflets 106, with the leaflet and skirt assembly secured to the inflow section IS and a portion of the connecting section CS. The assembly 100 can be effectively secured at the native aortic annulus. The overall construction of the assembly 100 is simple, and effective in promoting proper aortic valve function.

Figure 3:
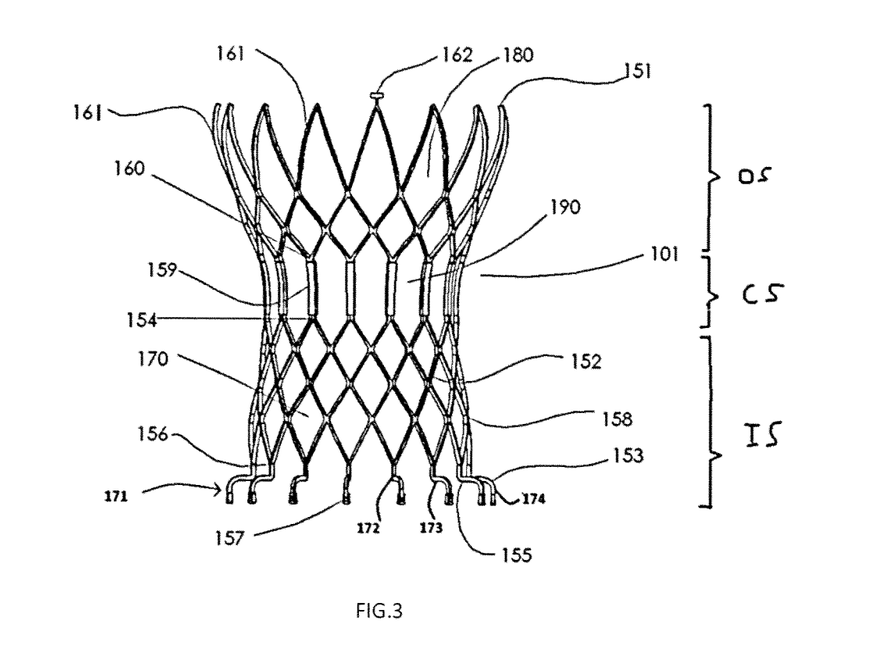
FIG. 3 is a perspective side view of the frame of the assembly of FIG. 1A.
Figure 4:
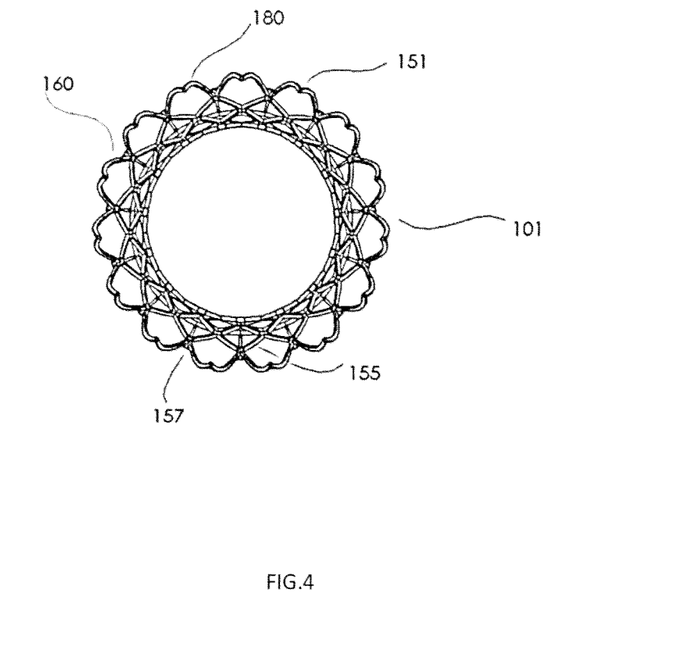
FIG. 4 is a top view of the frame of FIG. 3.
Figure 5:
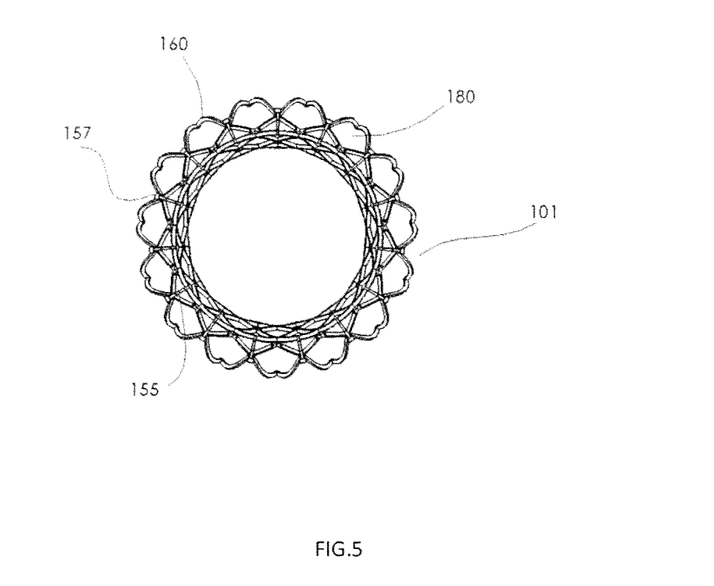
FIG. 5 is a bottom view of the frame of FIG. 3.

As shown in FIGS. 3-5, the inflow section IS and the outflow section OS of the frame 101 can be made of one continuous wire, and can be made from a thin wall biocompatible metallic element (such as stainless steel, Co—Cr based alloy, Nitinol™, Ta, and Ti etc.). As an example, the wire can be made from a Nitinol™ wire that is well-known in the art, and have a diameter of 0.02" to 0.04". The inner and outer sections IS and OS define open cells within the frame 101. Starting with the inflow section IS, the inflow section IS has a body portion that is made up by a plurality of annular rows of diamond-shaped cells 170 that are defined by a plurality of struts 152 connecting at apices 158 to encircle the cell 170. FIG. 3 shows three rows of staggered or alternating cells 170, although two or four or more rows of cells 170 can be provided. A plurality of flared legs 171 extends from the outer-most apices 156 of the cells 170 to form an annular flange of legs 171. Specifically, each leg 171 has a first part 172 which extends vertically from an apex 156 along the same plane as the struts 152 of the cell 170, and then transitions to a first bend 155 to a second part 173 which extends radially outwardly (perpendicular to the first part 172), and then transitions to a second bend 153 to a third part 174 which extends vertically (perpendicular to the second part 173) which terminates at an ear 157.

The outflow section OS has a body portion that is made up one row of diamond-shaped cells 170 that are similar to the cells 170 in the inflow section IS. Connection beams 159 of the connector section CS connect the apices 160 of the cells 170 in the outflow section OS with the apices 154 of the inflow section IS. Another row of cells 180 is provided in the outflow section OS downstream from the row of cells 170 for the outflow section OS. The cells 180 are formed by struts 161 connecting at apices (e.g., 151). The cells 180 can also be diamond-shaped but can be larger and shaped a little differently. The outflow end of the cells 180 terminate at apices 151, and ears 162 are provided at selected apices 151.

The connecting section CS comprises the beams 159 that connect corresponding apices (e.g., 154 and 160) of the cells 170 in the inflow section IS and the outflow section OS. Cells 190 are defined by the beams 159 and the struts of the cells 170 that are located at the boundaries of the inflow section IS and outflow section OS, and these cells 190 are generally shaped as a hexagon with two longer base sides defined by the beams 159 and four other shorter sides. These beams 159 can be made thicker (i.e., widened) by providing or cutting them to be thicker than the other struts.

The cells 170, 180 and 190 have different shapes and sizes because it is preferred that the cells 190 and 180 have less expansion force than the cells 170. The cells 170 on the inflow section IS are provided to be stiffer and less compressible than the cells 190 so as to ensure the expansion force needed for access to the annulus region when dealing with a calcified valve, while allowing the connecting section CS to be relatively easy to compress so that the connecting section CS can be retrieved during the deployment of the valve assembly. Also, the beam 159 is strong enough to withstand the deflection exerted from the commissure. Thus, the three sections IS, CS and OS are provided with the different cell size, cell shapes and beam width for the purpose of varying the flexibility and stiffness at the different sections IS, CS and OS.

Figure 9:
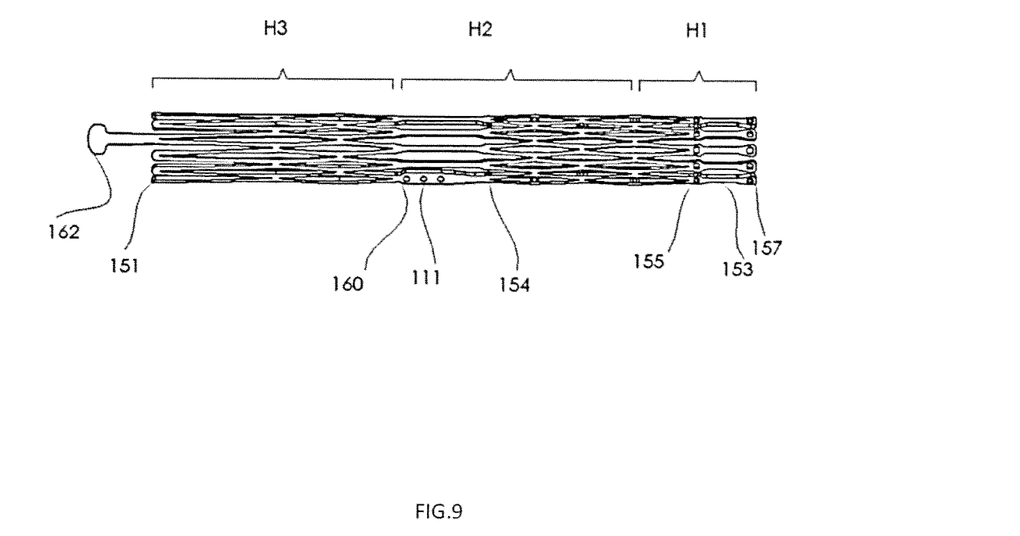
FIG. 9 is a side view of the frame of FIG. 3 shown in its compressed configuration.

The valve assembly 100 is intended for use as an aortic replacement valve for the following valve sizes: 23 mm, 26 mm, 29 mm, 32 mm and 35 mm. As such, the height H3 of the outflow section OS can be about 10-12 mm, the height H2 of the connecting section CS and a portion of the inflow section IS (see FIG. 1A) can be about 10-12 mm, and the height H1 of a portion of the inflow section IS can be about 10-12 mm. The three heights H1, H2 and H3 show the division of the frame 101 into three equally-divided lengths. As shown in FIG. 9, when the valve assembly 100 is in the compressed configuration, most of the valve assembly 100 along H3 and H2 can still be retrievable because of the compressibility of the connecting section CS, and this retrievable length is almost two-thirds of the overall length (H1+H2+H3) of the valve assembly 100. Also, as shown in FIG. 9, the legs 171 are straightened (instead of being bent into the parts 172, 173, 174 when in its deployed configuration) during delivery so that the row of legs 171 has a diameter that is the same as the diameter of the rest of the compressed frame 101, thereby ensuring that the valve assembly 100 has a low profile when crimped. When the inflow section IS is released from the delivery capsule 2010 (see below), the shape-memory characteristic of the material will cause the legs 171 to be bent to form the various parts 172, 173 and 174, thereby forming a row of legs 171 that has a diameter greater than the diameter of the remainder of the frame 101.

Figure 6:
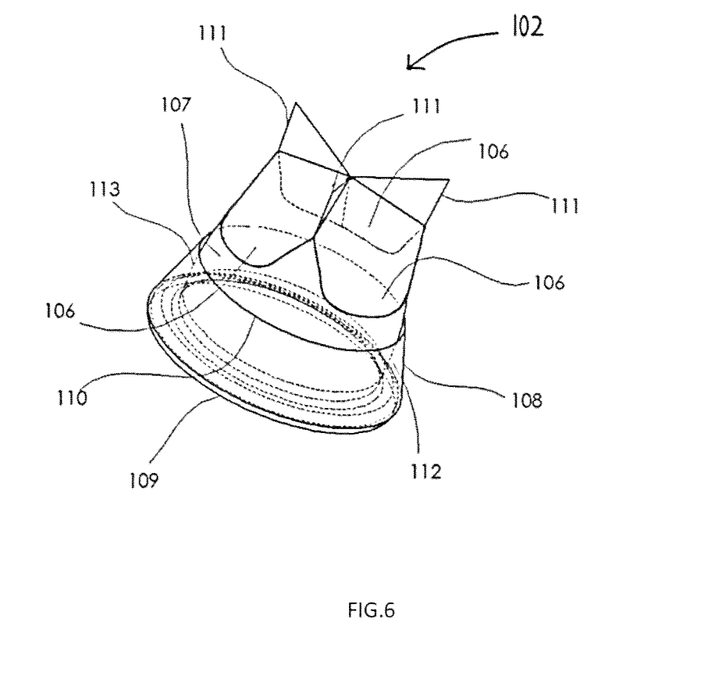
FIG. 6 is a perspective view of the leaflet assembly of the valve assembly of FIG. 1A.
Figure 7:
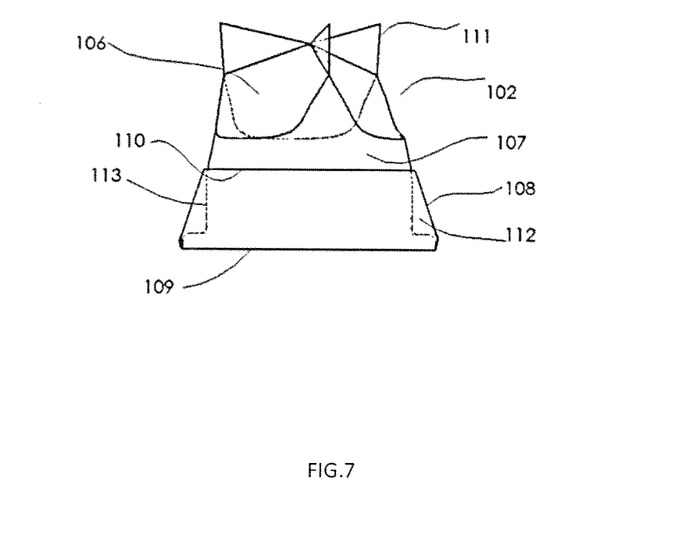
FIG. 7 is a side view of the leaflet assembly of FIG. 6.
Figure 8:
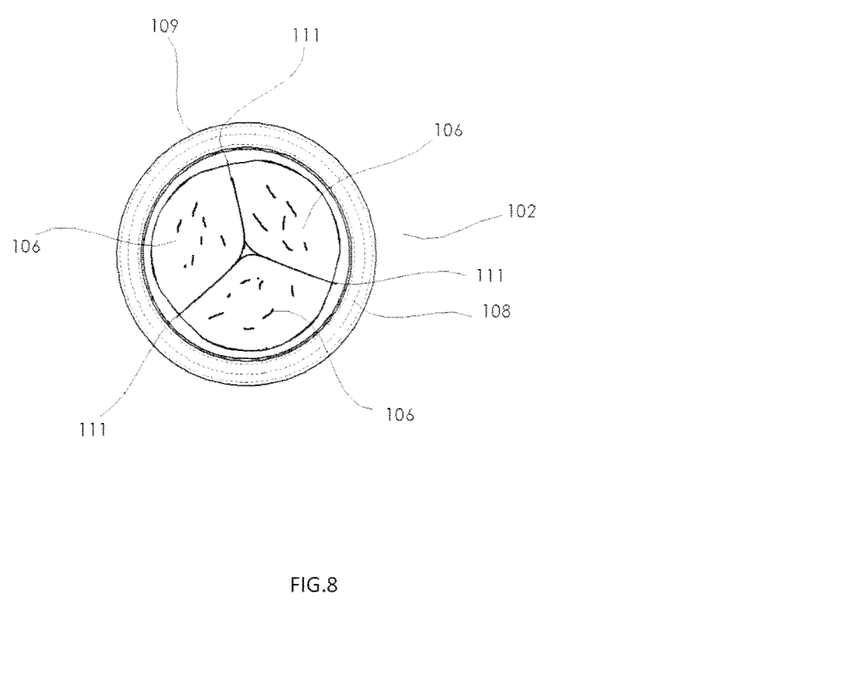
FIG. 8 is a top view of the leaflet assembly of FIG. 6.

The leaflet and skirt assembly 102 is shown in FIGS. 6-8, and it includes three leaflets 106 sewn together at the commissures 111. An inner tubular valve skirt 107 extends from the leaflets 106 to a flanged inflow skirt 109. The leaflets 106 and the inner valve skirt 107 (including a concealed portion 113) are sewn to the inside of the struts 152 of the cells 170 in the inflow section IS. As shown in FIG. 1A, the leaflets 106 are preferably positioned at the border between the connector section CS and the inflow section IS. The flanged inflow skirt 109 is formed by folding the skirt material over the ears 157 of the flanged legs 171. The skirt material that is folded over the ears 157 is then extended at an angle along the outer surface of the struts 152 to form an angled outer skirt or cuff section 108, which terminates at an annular stitch line 110. As a result of the folding over of the skirt material, an empty space 112 is defined between the concealed portion 113, the outer skirt 108, and the inflow skirt 109. As best shown in FIGS. 2 and 11C, the valve assembly 100 is preferably deployed at the native aortic annulus in a manner such that the native aortic annulus impinges against the outer skirt 108, with this portion of the outer skirt 108 (and the space 112 inside) acting both as a seal to prevent PVL, and as a buffer or cushion to protect the native annulus from impinging on the hard surface of the frame 101.

The skirt and leaflet material can be made from a treated animal tissue such as pericardium, or from biocompatible polymer material (such as PTFE, Dacron, etc.). The leaflets 106 and the skirts can also be provided with a drug or bioagent coating to improve performance, prevent thrombus formation, and promote endothelialization, and can also be treated (or be provided) with a surface layer/coating to prevent calcification.

In addition, the length of the inflow section IS and the connecting section CS can vary depending on the number of leaflets 106 supported therein. For example, in the embodiment illustrated in FIGS. 1A-8 where three leaflets 106 are provided, the length of the connector section CS can be 15-20 mm and the length of the inflow section IS can be 10-15 mm. If four leaflets 106 are provided, the respective lengths can be shorter, such that the length of the connector section CS can be 10-15 mm and the length of the inflow section IS can be 10-15 mm. These exemplary dimensions can be used for an assembly 100 that is adapted for use at the native aortic annulus for a generic adult.

The assembly 100 of the present invention can be compacted into a low profile and loaded onto a delivery system, and then delivered to the target location by a minimally invasive medical procedure, such as by the use of a delivery catheter through transapical, or transfemoral, or transaortic procedures. The assembly 100 can be released from the delivery system once it reaches the target implant site, and can expand to its normal (expanded) profile either by inflation of a balloon (for a balloon expandable frame 101) or by elastic energy stored in the frame 101 (for a device where the frame 101 is made of a self-expandable material).

FIGS. 10A-11C illustrate how the assembly 100 can be deployed through the aorta of a patient using a transfemoral delivery. The delivery system includes a delivery catheter having an outer shaft 2020 that extends through a core body 2035 inside a handle 2050 at its proximal end, and has a capsule 2010 provided at its distal end. The valve assembly 100 is contained in its compressed configuration inside the capsule 2010. The ears 162 of the outflow section OS are removably attached to ear hubs 2030 that are connected to an inner core 2025. The inner core 2025 extends through the outer shaft 2020, the capsule 2010 and the lumen defined by the valve assembly 100 to a distal tip 2015 that is at the distal-most part of the inner core 2025.

Figure 10A:
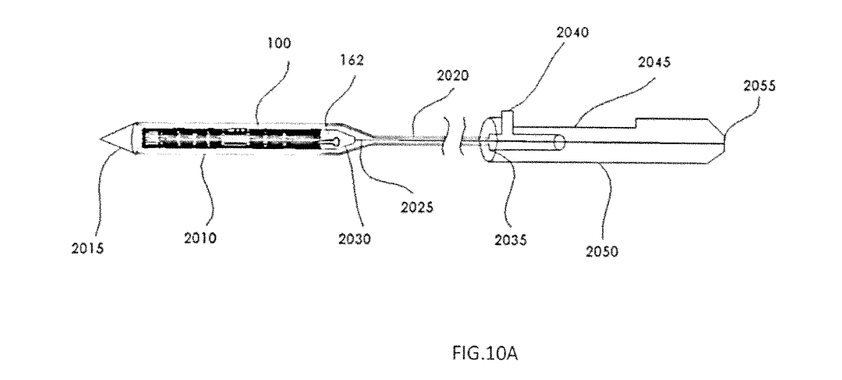
FIG. 10A illustrates a delivery system that can be used to deploy the valve assembly of FIG. 1A, shown with the valve assembly inside the capsule of the delivery catheter.
Figure 10B:
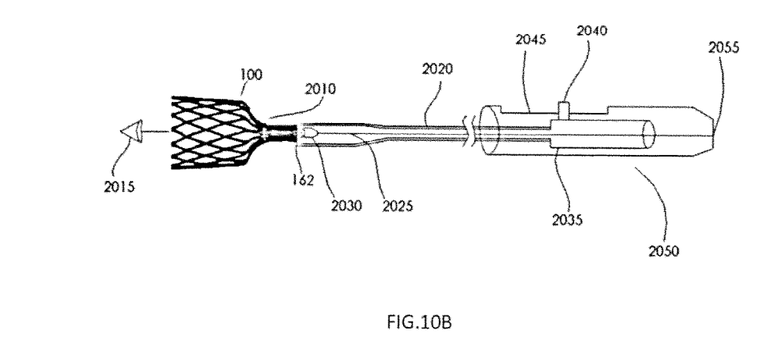
FIG. 10B illustrates the valve assembly being partially released from the capsule of FIG. 10A.
Figure 11A:
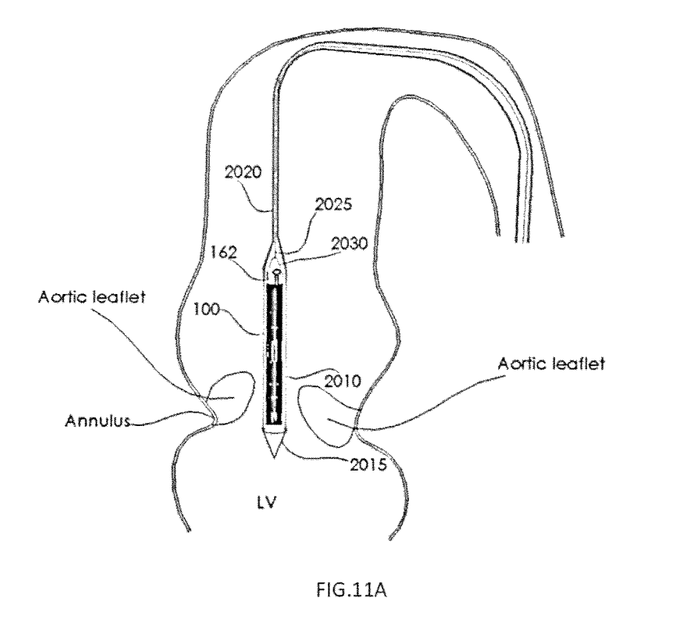
FIG. 11A illustrates the delivery of the delivery catheter of FIG. 10A with the valve assembly in its capsule to the location of the aortic annulus.
Figure 11B:
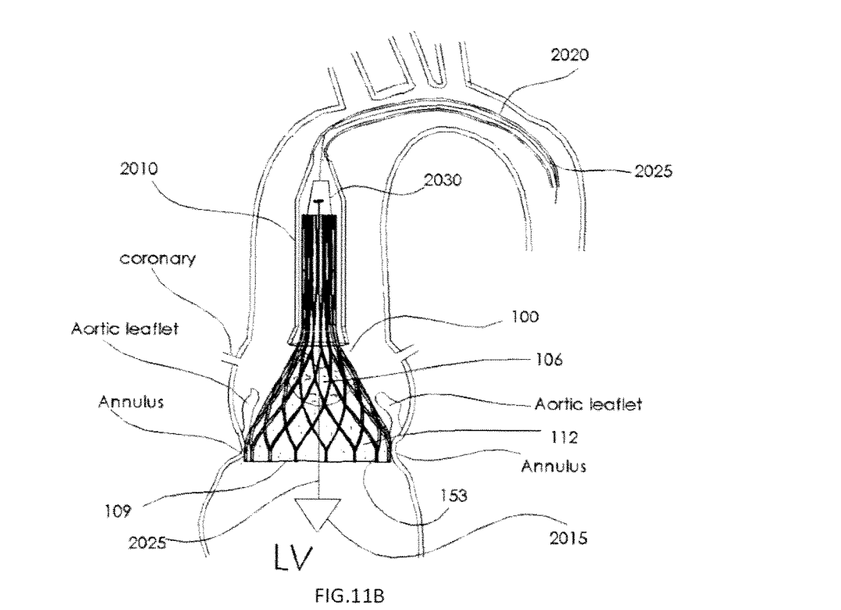
FIG. 11B illustrates the valve assembly partially expanded at the location of the aortic annulus.
Figure 11C:
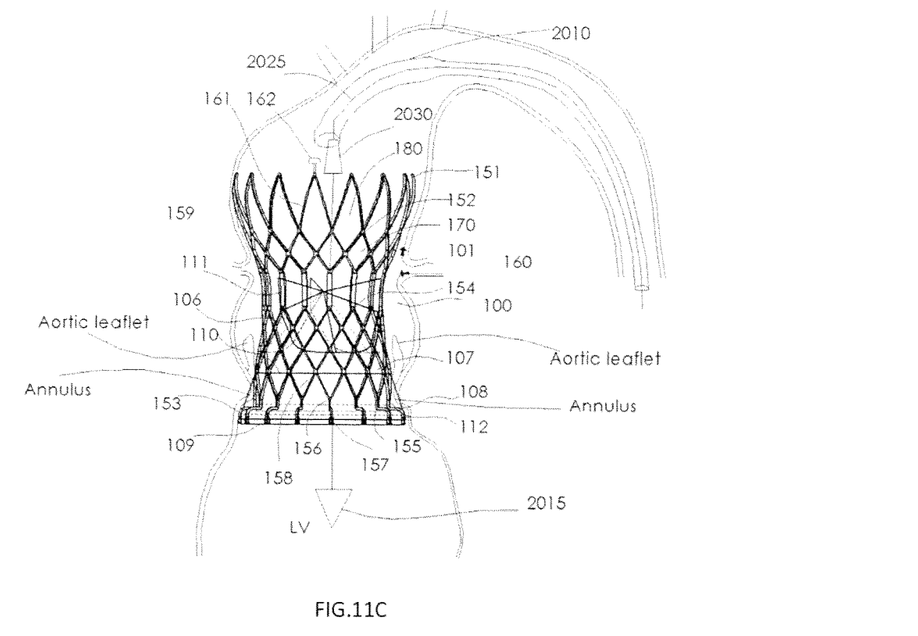
FIG. 11C illustrates the valve assembly fully deployed at the location of the aortic annulus.

As shown in FIGS. 10A and 11A, the valve assembly 100 is crimped and loaded inside the capsule 2010, and the capsule 2010 is delivered to the location of the aortic annulus so that the valve assembly 100 is positioned at the location of the native aortic annulus. As shown in FIGS. 10B and 11B, the capsule 2010 is slowly withdrawn to allow the inflow section IS to slowly expand at the location of the native aortic annulus. During this step, the distal tip 2015 and the capsule 2010 can still be pushed into the left ventricle or withdrawn from it to adjust the position of the valve assembly 100. The greater expansion force imparted by the cuff section formed by the inflow section IS will help to secure or anchor the cuff formed by the annular row of legs 171 at the aortic annulus. If the positioning is not accurate, the valve assembly 100 can still be retrievable into the capsule 2010 simply by reversing the deployment and advancing the capsule 2010 to crimp it and reload the valve assembly 100 back into the capsule 2010. Here, the varying flexibility allows the connecting section CS to be retrievable into the capsule 2010, while the inflow section IS still has sufficient expansion force to anchor or secure the valve assembly 100 at the aortic annulus.

Figure 10C:
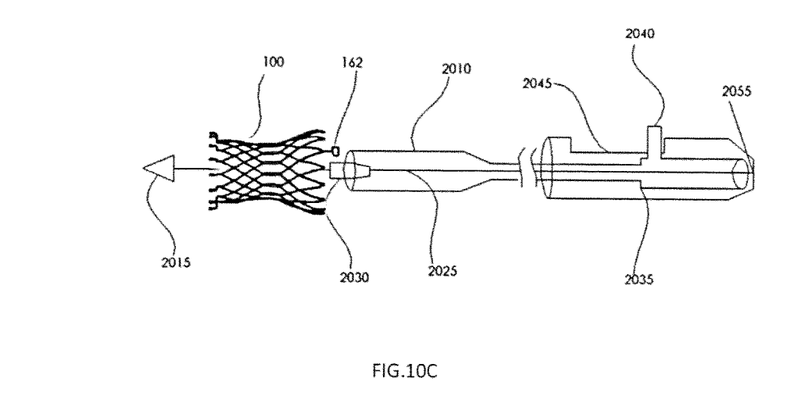
FIG. 10C illustrates the valve assembly being fully released from the capsule of FIG. 10A.

As shown in FIGS. 10C and 11C, further withdrawal of the capsule 2010 will release the remainder of the valve assembly 100. The ears 162 become disengaged from the ear hubs 2030, and the assembly 100 is completely expanded, and the entire delivery system can then be removed. As best shown in FIGS. 1B and 11C, the valve assembly 100 is deployed at the native aortic annulus in a manner such that the native aortic annulus impinges against the outer skirt 108, with this portion of the outer skirt 108 (and the space 112 inside) acting as a seal ring to prevent PVL.

The assembly 100 of the present invention provides a number of benefits which address the shortcomings described hereinabove.

First, the present invention provides improved access. The frame 101 has multiple zones, with the inflow section IS having the strongest expansion force to effectively expand the calcified leaflets and to secure the frame's position in the annulus. This is achieved by the condensed smaller cells 170 in the inflow section IS. In addition, the middle (connecting) section CS is to be deployed in the aortic sinus with no resistance to its expansion. It does not need the strong expansion but needs to support the force on the commissure generated by pressure on the prosthetic leaflets. Therefore, it is required to have minimum deflection in each valve closing cycle. This vertical rigidity is achieved in the present invention with a hexagon-shaped middle (connecting) section CS that has widened strut beams 159. This design increases the open space for later catheter access to the coronary artery while keeping its rigidity for supporting the commissure.

Second, the present invention allows for the valve assembly 100 to be easily resheathed. The present invention has an elongated hexagon-shaped connecting section CS which is relatively easier to collapse than the inflow section IS, which has smaller diamond-shaped cells, thereby making the valve assembly 100 retrievable even when deployed by up to two-thirds of its length. Meanwhile, the inflow section IS has a condensed cell design to ensure the expansion force needed for access even when dealing with a calcified valve.

Third, the present invention minimizes PVL. The present invention extends the frame 100 into the cuff region, which is made of the extended metal frame and tissue material wrapped around the inflow edge of the frame. During the crimping and loading of the valve assembly 100 into the delivery catheter, the inflow section IS is extended and the skirt material around it is stretched so that the profile is the same as the other tissue-covered sections of the frame 101, thereby resulting in no additional profile increase. Upon the release of the valve assembly 102 in situ, the extended frame section IS curls up to its preset shape and the tissue around it is folded back with it, thereby creating a soft cuff that functions to effectively seal against PVL.

FIGS. 12A, 12B and 13-15 illustrate a second embodiment of the present invention. The valve assembly 100A is essentially the same as the valve assembly 100 of the first embodiment except that the legs 174A of the inflow section IS have a reversed configuration, and the leaflet and skirt assembly 102A is configured to correspond to the configuration of the legs 174A. The connecting section CS and the outflow section OS of the valve assembly 100A can be the same for the embodiment shown in FIGS. 1-11C, so the same numerals are used in both embodiments to represent the same or corresponding elements.

Figure 13:
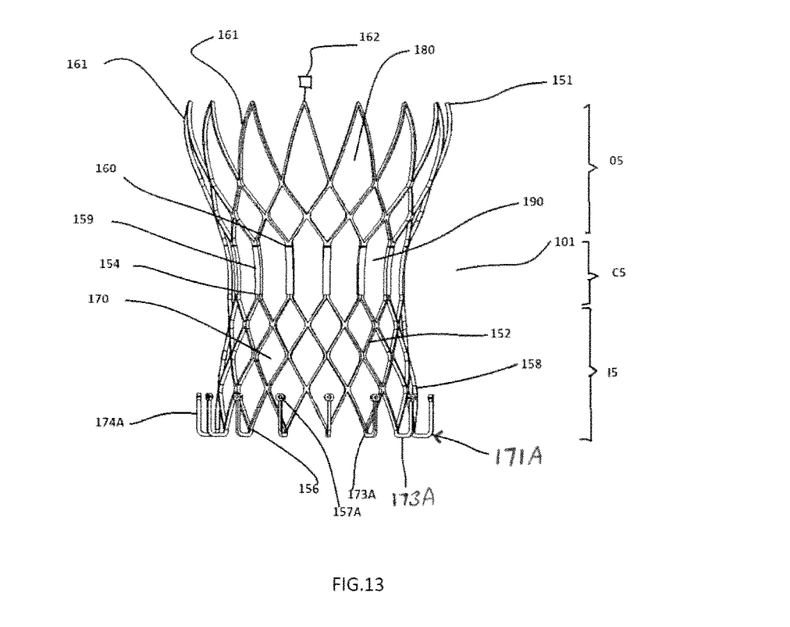
FIG. 13 is a perspective side view of the frame of the assembly of FIG. 12A.

As with the first embodiment, a plurality of flared legs 171A extends from the outer-most apices 156 of the cells 170 to form an annular flange of legs 171A. Specifically, each leg 171A has a first part 173A which extends radially outwardly (perpendicular to the plane of the inflow section IS), and then transitions to a second part 174A which extends vertically (perpendicular to the first part 173A) upwardly and which terminates at an ear 157A. The second part 174A is generally parallel to the plane of the inflow section IS. The elements 173A, 174A and 157A correspond to similar elements 173, 174 and 157, respectively.

Figure 12A:
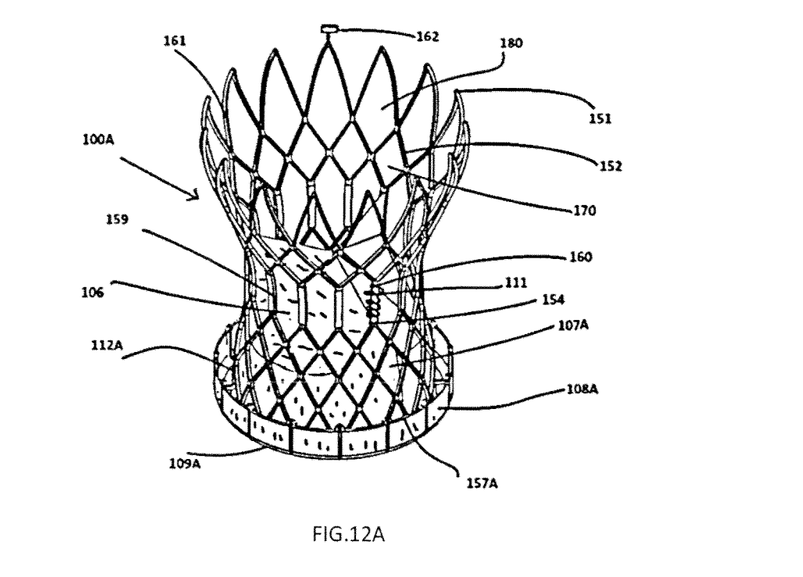
FIG. 12A is a perspective side view of an aortic valve assembly according to another embodiment of the present invention shown in an expanded configuration.
Figure 12B:
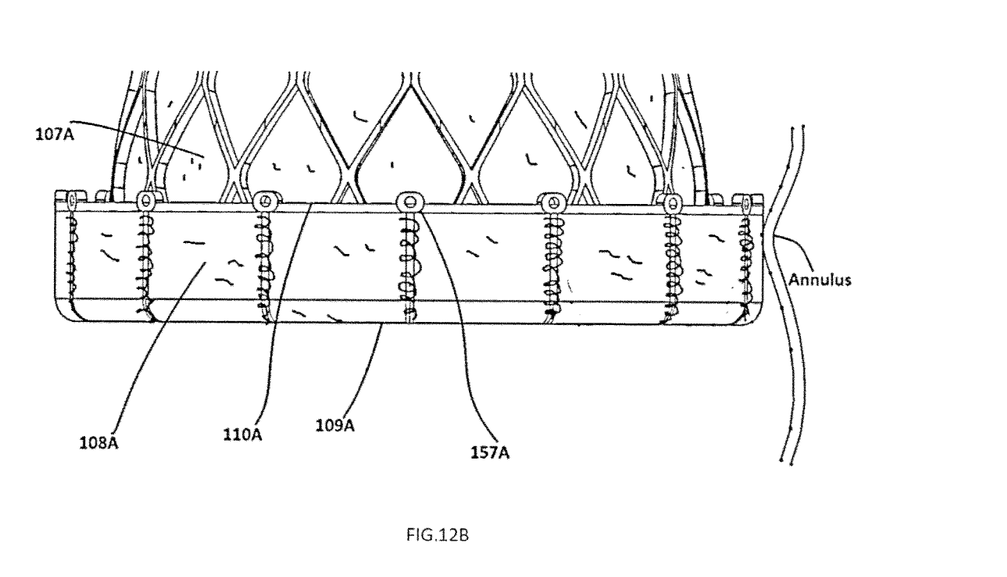
FIG. 12B is an enlarged side view of the inflow end of the assembly of FIG. 12A.
Figure 14:
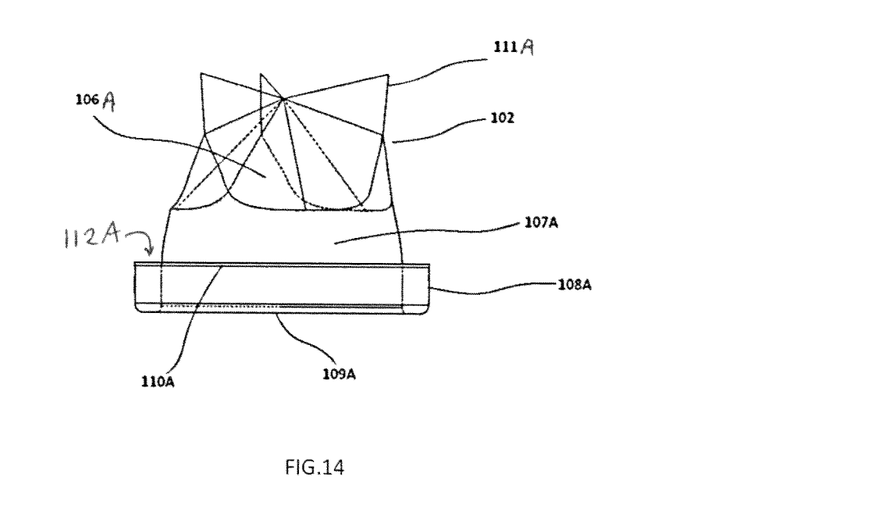
FIG. 14 is a side view of the leaflet assembly of the valve assembly of FIG. 12A.
Figure 15:
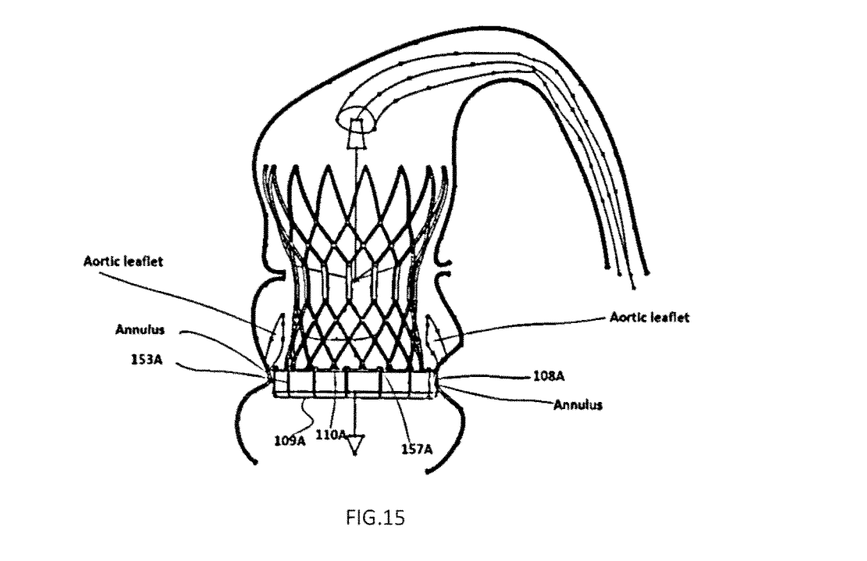
FIG. 15 illustrates the valve assembly of FIG. 12A fully deployed at the location of the aortic annulus.

The leaflet and skirt assembly 102A is shown in FIG. 14, and it includes three leaflets 106A sewn together at the commissures 111A. An inner tubular valve skirt 107A extends from the leaflets 106A to a flanged inflow skirt 109A. The leaflets 106A and the inner valve skirt 107A are sewn to the inside of the struts 152 of the cells 170 in the inflow section IS. As shown in FIG. 12A, the leaflets 106A are preferably positioned at the border between the connector section CS and the inflow section IS. The flanged inflow skirt 109A is formed by folding the skirt material over the parts 173A and 174A of the flanged legs 171A, and then secured to the ears 157A to form an outer skirt or cuff section 108A, which terminates at an annular stitch line 110A. As a result of the folding over of the skirt material, an empty space 112A is defined between the outer skirt 108A, and the inner valve skirt 107A. As best shown in FIG. 12B, the valve assembly 100A is preferably deployed at the native aortic annulus in a manner such that the native aortic annulus impinges against the outer skirt 108A, with this portion of the outer skirt 108A (and the space 112A inside) acting both as a seal to prevent PVL, and as a buffer or cushion to protect the native annulus from impinging on the hard surface of the frame 101.

The second embodiment bends the legs 171A in an opposing way, with diamond cells underneath them. The cuff section defined by the outer skirt 108A would be strong from the support of the main frame 107A, and yet provide a soft cuff by the tissues sutured around the bent legs 171A. The crimped profile is the same as main frame since the bent legs 171A will be straightened out in the chilled saline and loaded into the delivery catheter. As with the first embodiment, the folding-over to form a cuff will occur at the body temperature upon deployment. With this second embodiment, the cuff section can be deployed directly in the annulus to expand and seal the calcified annulus.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A heart valve assembly, comprising:
a frame that assumes a compressed configuration and an expanded configuration, the frame comprising an inflow section, an outflow section, and a connecting section that is located between the inflow section and the outflow section, the inflow section having a plurality of legs that extend radially outwardly in the expanded configuration, and wherein the connecting section has a greater flexibility than the inner section;
a leaflet and skirt assembly having a plurality of leaflets coupled to the connecting section, a valve skirt extending from the leaflets towards the inflow section of the frame, and a cuff section, wherein the legs and the cuff section define a cuff in the expanded configuration for engagement with a native annulus; and
wherein each of the plurality of legs has a first part which extends vertically from the inflow section along the same plane as the frame, and then transitions to a first bend to a second part which extends radially outwardly and perpendicularly to the first part, and then transitions to a second bend to a third part which perpendicular to the second part, the third part terminating in an ear.

2. The assembly of claim 1, wherein the frame is made of a shape memory material.

3. The assembly of claim 1, wherein the cuff section comprises a concealed portion that extends from the valve skirt and has a flanged inflow skirt that is folded over the ears of the legs, and defining an angled outer skirt that extends at an angle along the outer surface of the inflow section and which terminates at an annular stitch line, with an empty space is defined between the concealed portion, the outer skirt, and the inflow skirt.

4. A heart valve assembly, comprising:
a frame that assumes a compressed configuration and an expanded configuration, the frame comprising an inflow section, an outflow section, and a connecting section that is located between the inflow section and the outflow section, the inflow section having a plurality of legs that extend radially outwardly in the expanded configuration, and wherein the connecting section has a greater flexibility than the inner section;
a leaflet and skirt assembly having a plurality of leaflets coupled to the connecting section, a valve skirt extending from the leaflets towards the inflow section of the frame, and a cuff section, wherein the legs and the cuff section define a cuff in the expanded configuration for engagement with a native annulus; and
wherein each of the plurality of legs has a first part which extends radially outwardly and perpendicularly to the plane of the inflow section, and then transitions to a second part which extends vertically and perpendicular to the first part such that the second part is generally parallel to the plane of the inflow section.

5. The assembly of claim 4, wherein the cuff section comprises a flanged inflow skirt that is formed by folding the inflow skirt over the first and second parts to form an outer skirt which terminates at an annular stitch line, with an empty space defined between the outer skirt and the inflow skirt.

6. The assembly of claim 1, wherein the frame is comprised of cells, with the cells in the connecting section having a different size from the cells in the inflow section.

7. The assembly of claim 1, wherein the combined length of the connecting section and the inflow section is about two-thirds the length of the entire frame.

8. A heart valve assembly, comprising:
a frame that assumes a compressed configuration and an expanded configuration, the frame comprising an inflow section, an outflow section, and a connecting section that is located between the inflow section and the outflow section, the inflow section having a plurality of legs; and
a leaflet and skirt assembly having a plurality of leaflets coupled to the connecting section, a valve skirt extending from the leaflets towards the inflow section of the frame, and a cuff section, wherein the legs and the cuff section define a cuff in the expanded configuration for engagement with a native annulus;
wherein the plurality of legs define an annular flange of legs that has the same diameter as the remainder of the frame when the frame and the legs are in the compressed configuration, and wherein the plurality of legs extend radially outwardly in the expanded configuration so that the flange of legs has a greater diameter than the remainder of the frame in the expanded configuration; and
wherein each of the plurality of legs has a first part which extends vertically from the inflow section along the same plane as the frame, and then transitions to a first bend to a second part which extends radially outwardly and perpendicularly to the first part, and then transitions to a second bend to a third part which perpendicular to the second part, the third part terminating in an ear.

9. The assembly of claim 8, wherein the frame is made of a shape memory material.

10. The assembly of claim 8, wherein the cuff section comprises a concealed portion that extends from the valve skirt and has a flanged inflow skirt that is folded over the ears of the legs, and defining an angled outer skirt that extends at an angle along the outer surface of the inflow section and which terminates at an annular stitch line, with an empty space is defined between the concealed portion, the outer skirt, and the inflow skirt.

11. A heart valve assembly, comprising:
a frame that assumes a compressed configuration and an expanded configuration, the frame comprising an inflow section, an outflow section, and a connecting section that is located between the inflow section and the outflow section, the inflow section having a plurality of legs;

a leaflet and skirt assembly having a plurality of leaflets coupled to the connecting section, a valve skirt extending from the leaflets towards the inflow section of the frame, and a cuff section, wherein the legs and the cuff section define a cuff in the expanded configuration for engagement with a native annulus;

wherein the plurality of legs define an annular flange of legs that has the same diameter as the remainder of the frame when the frame and the legs are in the compressed configuration, and wherein the plurality of legs extend radially outwardly in the expanded configuration so that the flange of legs has a greater diameter than the remainder of the frame in the expanded configuration; and wherein each of the plurality of legs has a first part which extends radially outwardly and perpendicularly to the plane of the inflow section, and then transitions to a second part which extends vertically and perpendicular to the first part such that the second part is generally parallel to the plane of the inflow section.

12. The assembly of claim 11, wherein the cuff section comprises a flanged inflow skirt that is formed by folding the inflow skirt over the first and second parts to form an outer skirt which terminates at an annular stitch line, with an empty space defined between the outer skirt and the inflow skirt.

13. The assembly of claim 8, wherein the frame is comprised of cells, with the cells in the connecting section having a different size from the cells in the inflow section.

14. The assembly of claim 8, wherein the combined length of the connecting section and the inflow section is about two-thirds the length of the entire frame.

15. The assembly of claim 4, wherein the frame is made of a shape memory material.

16. The assembly of claim 4, wherein the frame is comprised of cells, with the cells in the connecting section having a different size from the cells in the inflow section.

17. The assembly of claim 4, wherein the combined length of the connecting section and the inflow section is about two-thirds the length of the entire frame.

18. The assembly of claim 11, wherein the frame is made of a shape memory material.

19. The assembly of claim 11, wherein the frame is comprised of cells, with the cells in the connecting section having a different size from the cells in the inflow section.

20. The assembly of claim 11, wherein the combined length of the connecting section and the inflow section is about two-thirds the length of the entire frame.

* * * * *